United States Patent [19]

Rogel

[11] Patent Number: 5,906,583

[45] Date of Patent: May 25, 1999

[54] AUTOMATIC CARDIOMETER

[75] Inventor: Dan Rogel, Haifa, Israel

[73] Assignee: R.Z. Comparative Diagnostics Ltd., Haifa, Israel

[21] Appl. No.: 08/914,808

[22] Filed: Aug. 20, 1997

[51] Int. Cl.$^6$ .................................................. A61B 5/0452
[52] U.S. Cl. ........................................................... 600/515
[58] Field of Search ..................................... 600/509, 515, 600/516, 517, 523; 128/906, 920, 923, 924

[56] References Cited

U.S. PATENT DOCUMENTS

| | | | |
|---|---|---|---|
| 3,759,248 | 9/1973 | Valiquette | 600/516 |
| 5,456,261 | 10/1995 | Luczyk | 600/515 |
| 5,473,537 | 12/1995 | Glazer et al. | 128/920 |

*Primary Examiner*—William E. Kamm
*Attorney, Agent, or Firm*—Mark M. Friedman

[57] ABSTRACT

A device and method for user's ECG self monitoring and real time analysis are provided. The device comprises: (a) a sensing element and a processing element for recording and storing a first ECG signal from the user during a first time interval and recording a second ECG signal from the same user during a second time interval; (b) a comparing element for comparing the second ECG signal to the first ECG signal; (c) a logical decision element for making a logical decision based on the comparison and providing a recommendation to the user of a step he should take. According to another embodiment, the device includes: (a) ten sensing elements and a processing element for simultaneously recording twelve ECG signals from the user during a first time interval and simultaneously recording twelve ECG signals from the user during a second time interval; (b) a comparing element for comparing each of the ECG signals recorded during the second time interval to a respective ECG signal recorded during the first time interval so as to provide twelve delta values; (c) a logical decision element for making a logical decision based on the delta values and providing a recommendation to the user of a step he should take.

35 Claims, 8 Drawing Sheets

(a) $\Delta (STL)_i = (STL)_{oi} - (STL)_{ti}$

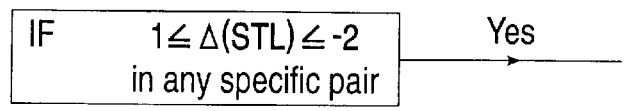

IF $1 \leq \Delta(STL) \leq -2$ in any specific pair → Yes → K = K+2

(b) $\Delta (SOT)_i = (SOT)_{oi} - (SOT)_{ti}$

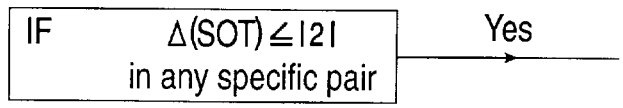

IF $\Delta(SOT) \leq |2|$ in any specific pair → Yes → K = K+2

(c) $\Delta (Q\ Int)_i = (Q\ Int)_{ti} - (Q\ Int)_{oi}$

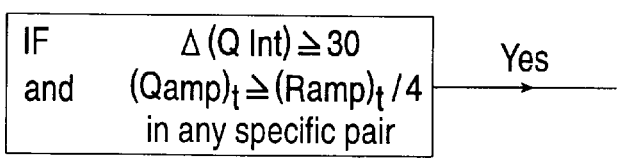

IF $\Delta(Q\ Int) \geq 30$ and $(Qamp)_t \geq (Ramp)_t /4$ in any specific pair → Yes → K = K+2

(d) 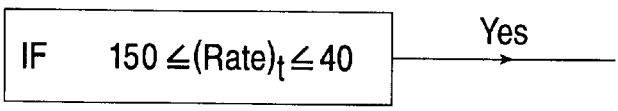

IF $150 \leq (Rate)_t \leq 40$ → Yes → K = K+2

(e) $\Delta (ARTH) = (ARTH)_t / (ARTH)_o$

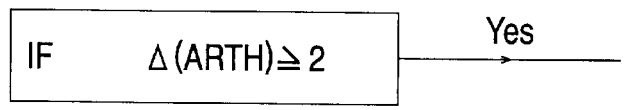

IF $\Delta(ARTH) \geq 2$ → Yes → K = K+2

FIG. 6

AUTOMATIC CARDIOMETER

FIELD AND BACKGROUND OF THE INVENTION

The present invention relates to a device and method for user's ECG self-examinations. More particularly, the present invention relates to a portable interactive ECG monitor and analyzer for real time guidance of a user.

Portable ECG monitors for personal use are well known in the art. Examples of such ECG monitors are disclosed in U.S. Pat. Nos. 5,181,519 and 5,226,424, and in PCT App. No. WO 93/19667.

Most of the disclosed inventions provide a portable ECG monitor unit for sensing ECG data of a user, and transmitting the data to a central ECG monitoring station for analysis via telephone lines. Thus, when the user feels discomfort he is expected to record an ECG signal and to send the information to the central monitoring station for analysis. However, such ECG services are usually very expensive, and therefore are purchased only by a small percentage of the population, usually those which already had experienced a serious heart event in the past.

There is thus a widely recognized need for, and it would be highly advantageous to have, a simple and reliable device and method which provide immediate and convenient service for the entire population, including healthy users.

It would be advantageous to have such device and method which enable usually healthy users to make a right decision at critical moments of their life—when they have chest pains or uncomfortable feelings before—damages to the heart become irreversible.

It would be further advantageous to have such home device and method for providing such service for the hole family.

Specifically, there is a widely recognized need for, and it would be highly advantageous to have, a device and method for independent analysis of ECG signals by a user which provide the user a real time guidance of the appropriate step he should take.

Further, it would be highly advantageous to have a portable interactive ECG device which records a first ECG signal at a first time interval, then records a second ECG signal at a substantially different second time interval—usually when the user feels discomfort, and compares the first and second signals so as to provide real-time information on significant changes of heart function when such changes occur.

Further, there is a widely recognized need for, and it would be highly advantageous to have, an interactive ECG device which includes a logical decision making unit for analyzing the output of such analysis along with other information provided interactively by the user so as to immediately provide an appropriate recommendation to the user of the steps he should take.

Further, it would be advantageous to have such device and method which utilizes twelve leads ECG.

SUMMARY OF THE INVENTION

According to the present invention there are provided device and method for user's ECG self-monitoring and analysis. The device comprises: (a) a sensing element and a processing element for recording and storing a first ECG signal from the user during a first time interval and recording a second ECG signal from the same user during a second time interval; (b) a comparing element for comparing the second EGG signal to the first EGG signal; (c) a logical decision element for making a logical decision based on the comparison and providing a recommendation to the user of a step he should take. Preferably, the processing element calculates a first ECG parameter of the first ECG signal and a second respective ECG parameter of the second ECG signal and the comparing element compares the first and second ECG parameters. Preferably, the first and second ECG parameters are selected from the group consisting of: (a) ST level parameters; (b) sign of T-wave; (c) amplitude of Q wave; (d) width of Q wave; (e) heart rate; and (f) heart rhythm.

According to further preferred features of the invention described below, the device includes a display element and a keyboard for interactively communicating with the user. Preferably, the display element asks the user a list of questions, and the logical decision is made and the recommendation is given based on the user's answers.

Preferably, the device includes an instruction panel for instructing the user how to determine his risk factor. The display unit asks the user for his risk factor so that the decision is made and the recommendation is given based on the risk factor.

According to another embodiment, the device includes: (a) ten sensing elements and a processing element for simultaneously recording twelve ECG signals from the user during a first time interval and simultaneously recording twelve ECG signals from the user during a second time interval; (b) a comparing element for comparing each of the ECG signals recorded during the second time interval to a respective ECG signal recorded during the first time interval so as to provide twelve delta values; (c) a logical decision element for making a logical decision based on the delta values and providing a recommendation to the user of a step he should take. Preferably, the logical decision element analyzes specific pairs of said delta values. The twelve ECG signals recorded during the first and second time intervals are designated as I, II, III, (AVR), (AVL), (AVF), V1, V2, V3, V4, V5, and V6. The specific pairs are preferably selected from the group consisting of: (a) I and (AVL); (b) II and III; (c) III and (AVF); (d) (AVF) and V1; (e) V1 and V2; (f) V2 and V3; (g) V3 and V4; (h) V4 and V5; and (i) V5 and V6. Preferably, the processing element calculates an ECG parameter of each of the twelve ECG signals recorded during the first time interval and a respective ECG parameter of each of the twelve ECG signals recorded during the second time interval and the twelve delta values are calculated by comparing the ECG parameters to the respective ECG parameters. Preferably, the EGG parameters and the respective ECG parameters are selected from the group consisting of: (a) ST level parameters; (b) sign of T-wave; (c) amplitude of Q wave; (d) width of Q wave; (e) heart rate; and (f) heart rhythm.

Further according to the present invention there is provide a method for estimating the R-apex location of a specific QRS complex recorded during a specific time interval, comprising: (a) finding the R-apex location of the specific QRS complex for each of a plurality of simultaneously recorded ECG signals so as to obtain a plurality of R-apex locations; (b) if at least a predetermined number of the R-apex locations is within a predetermined time range, then estimating the R-apex location of the specific QRS complex to be an average of the R-apex locations of the at least predetermined number.

According to another embodiment, the method comprises: (a) finding the R-apex locations of QRS complexes in a recorded ECG signal; (b) performing said finding of R-apex locations for each of a plurality of simultaneously recorded ECG signals so as to obtain a matrix of R-apex locations, wherein each of said matrix's rows relates to a specific recorded ECG signal and wherein each of said matrix's columns relates to a specific QRS complex; (c) for each of the matrix's columns performing: if at least a predetermined number of R-apex locations are within a predetermined time range, then estimating the R-apex location of the specific ECG complex to be an average of the at R-apex locations of the at least predetermined number.

BRIEF DESCRIPTION OF THE DRAWINGS

The invention is herein described, by way of example only, with reference to the accompanying drawings, wherein:

FIG. 6 illustrates preferred steps of a method according to the present invention including analysis based on the examination of ST-level, sign of T wave, Interval and amplitude of Q wave and amplitude of R wave, heart rate and heart rhythm.

DESCRIPTION OF THE PREFERRED EMBODIMENTS

The present invention is of a device and method for performing user's ECG self-examination. Specifically, the present invention provides a portable interactive ECG monitor and analyzer for real time guidance of a user, and a method for personally carrying out an ECG examination.

The principles and operation of apparatus and method according to the present invention may be better understood with reference to the drawings and the accompanying description.

Figure 1:
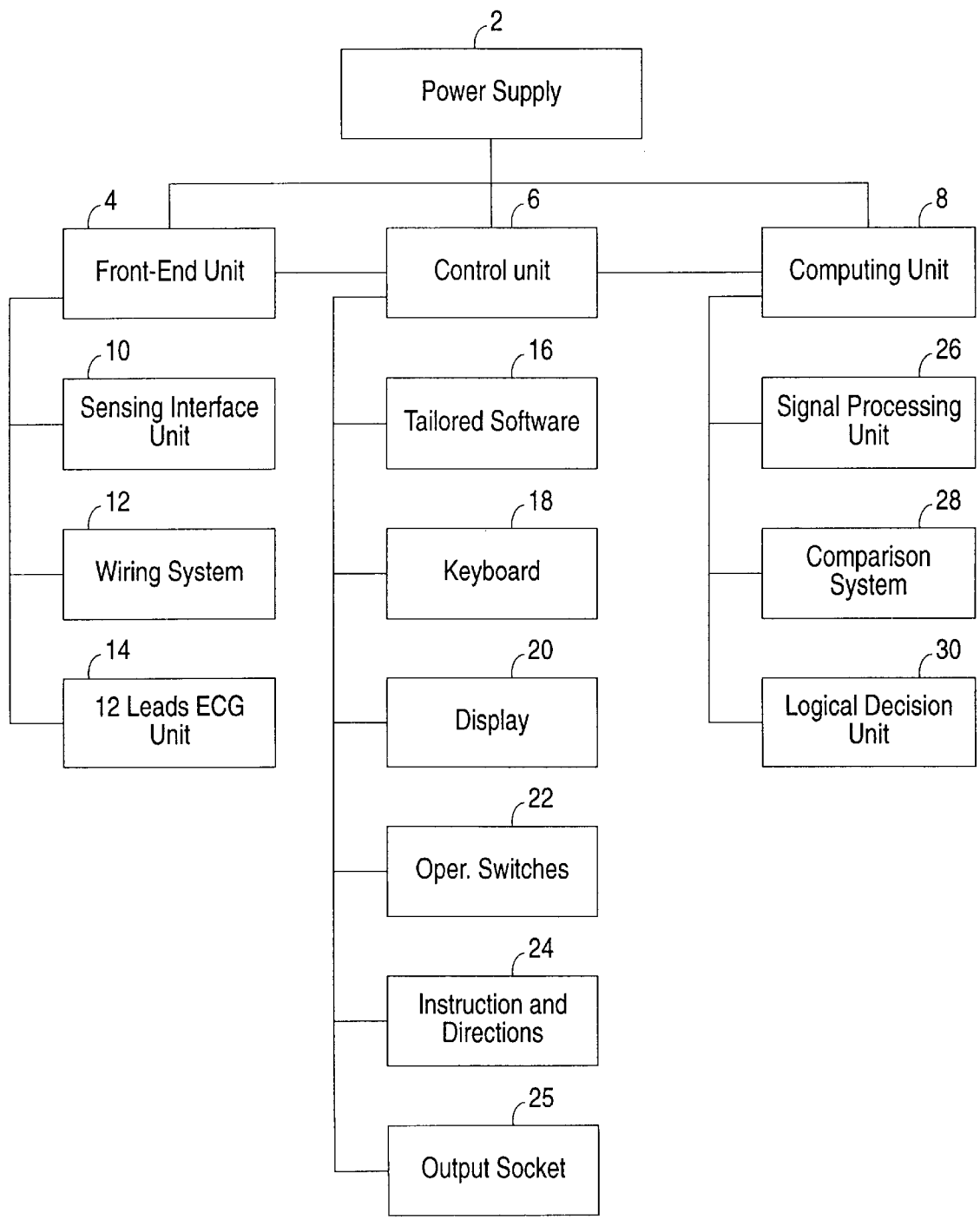
FIG. 1 is a preferred schematic block diagram of a device according to the present invention.

Referring now to the drawings, FIG. 1 illustrates a schematic block diagram of a device according to the present invention. The device preferably includes a front end unit 4, a control unit 6, a computing unit 8 and a power supply unit 2. Front end unit 4 includes a sensing interface unit 10 for sensing electrical potentials (voltage) across the user's body and a wiring system 12 for transferring the voltage signals to a twelve-leads ECG unit 14.

Sensing interface unit 10 preferably includes ten sensors for providing twelve ECG signals at a given time interval (twelve-leads ECG). Preferably, the sensors are mechanically interconnected by means of connecting elements such as straps for providing a predetermined sensor assembly configuration so as to ensure that the sensors' positions on the user's body are substantially repeatable when performing a new measurement. The connecting elements may be disposable. The connecting elements may be of various sizes so as to provide sensor assembly configurations specifically adapted for patients of various sizes. The specific sensor assembly configuration is preferably individually adjustable by the user. Wiring system 12 preferably includes ten wires for transferring the signals sensed by the ten sensors to computing unit 8.

Front end unit 4 preferably includes twelve-leads ECG unit 14. Twelve-leads ECG unit 14 receives and samples the signals sensed by sensing interface unit 10, amplifies and filters the signals, organizes the information so as to provide simultaneous twelve ECG signals over a predetermined time interval, and sends the information for further processing to computing unit 8.

Control unit 6 for controlling the operation of the device preferably includes a specifically tailored software 16 for database management and time table management, a keyboard 18 and a display unit 20 for interactive communication with the user, operational switches 22 for deterministic operations such as on/off, and instruction panels 24 attached to the device for directing the user. Preferably, control unit 6 further includes an output socket 25 for transferring stored information which can later be analyzed by means of another device, for example, in a hospital.

Figure 8:
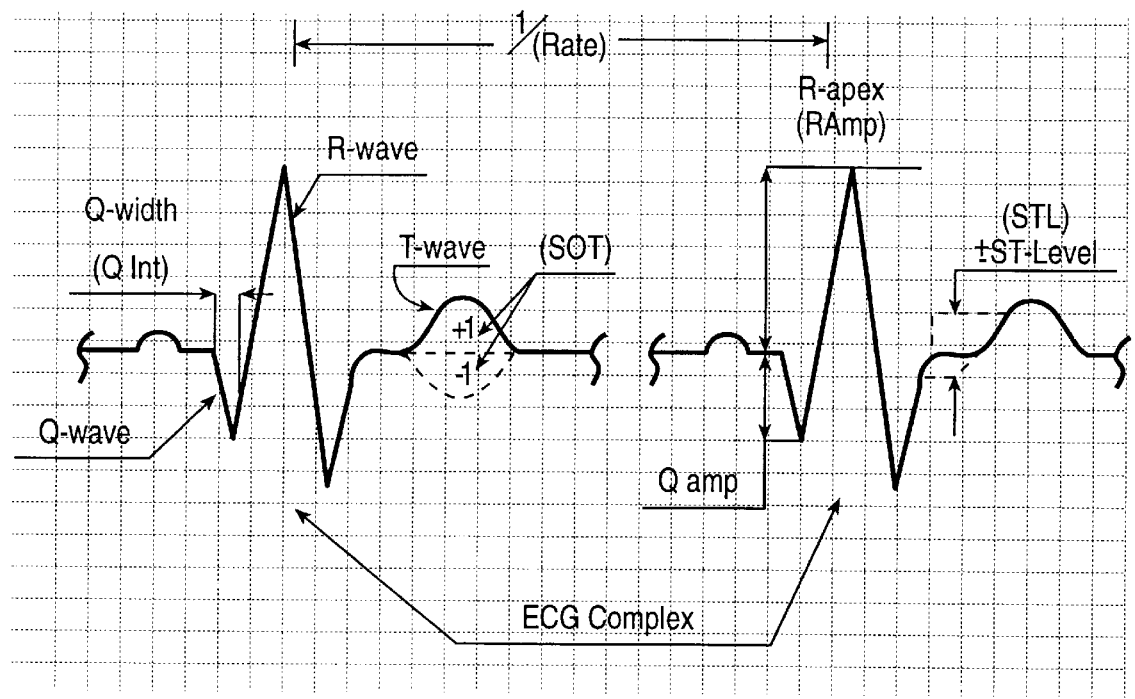
FIG. 8 illustrates preferred parameters of an ECG signal which are analyzed according to the present invention.

Computing unit 8 preferably includes a signal processing unit 26 which receives and stores information including signals transferred from front end unit 4, and employs signal processing algorithms and statistical analysis methods for determining the value of various ECG parameters such as ST-level, sign of T-wave, amplitude and width of Q wave (see also FIG. 8), R-apex, heart rate and heart rhythm based on the received signals.

Preferably, signal processing unit 26 performs parallel processing of twelve ECG signals provided by the ten sensors. Further, signal processing unit 26 preferably calculates secondary parameters such as J-point and R-apex location. The calculated parameters are stored within memory elements for further processing.

Computing unit 8 further includes a comparison system 28 for comparing the parameters of a new ECG signal to the parameters of a base line ECG signal. Comparing system 28 retrieves the stored parameters of each ECG signal and preferably subtracts the calculated parameters of a new ECG signal from the calculated parameters of a base line ECG signal. The results of the subtraction are stored within memory elements for further processing.

Computing unit 8 further includes logical decision unit 30 for making a decision based on the results obtained by comparison system 28 and other information interactively provided by the user.

Power supply unit 2 preferably includes chargeable batteries.

Figure 2:
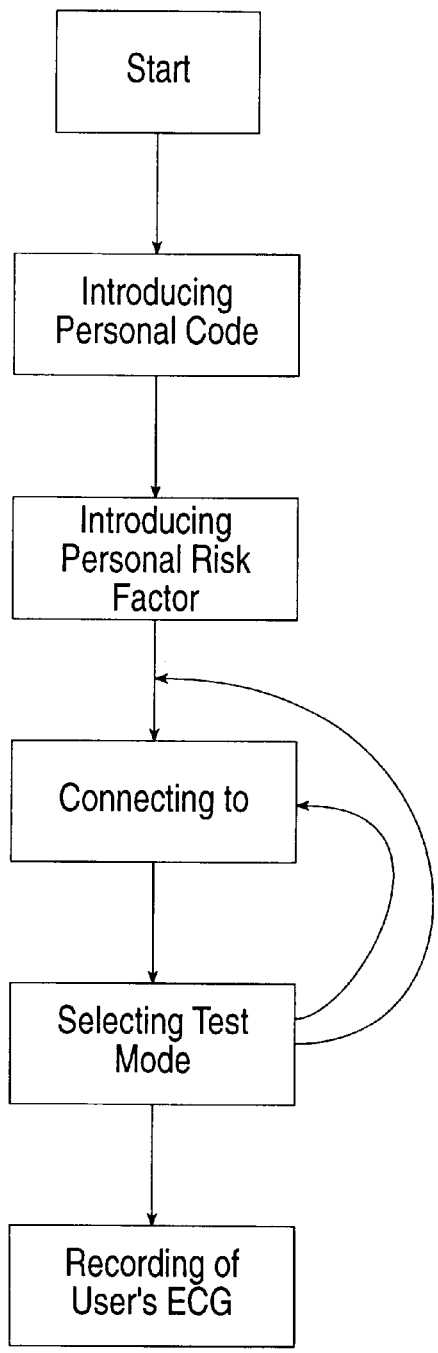
FIG. 2 is a schematic block diagram which illustrates a preferred first step of a method according to the present invention including introduction of a user's personal risk factor before carrying out an ECG measurement.

Referring now to FIG. 2, a first step of a method according to the present invention preferably includes the following procedure: The user turns on the device by means of switches 22. Display unit 20 then asks the user for his personal code. The user uses keyboard 18 for introducing his personal code. Different user's may use the device by introducing different personal codes. Thus, the device may serve several users within a family.

Display unit 20 then asks the user for his personal risk factor. Preferably, the user determines his personal risk factor according to a list of questions presented on instruction panel 24. The list of questions may include, for example, the following questions: (1) do you smoke?; (2) is there any hereditary heart problem within your family?; (3l) is your cholesterol level high?; (4) is your blood pressure level high?; (5) is your age above 40?. According to the answers provided, the user is instructed to determine his risk factor (R) to be, for example, 0, 1 or 2. Display unit 20 then asks the user to wear the sensor assembly, thereby automatically attaching the sensors to his body. As mentioned above, the device preferably utilizes a commonly used twelve leads ECG, wherein four sensors are attached to the user's limbs so as to provide 6 ECG signals commonly designated as I, II, III, (AVR), (AVL), and (AVF), and six sensors are attached to the user's chest so as to provide six ECG signals commonly designated as V1, V2, V3, V4, V5 and V6.

The display unit then asks the user to select a test mode. After the user selects a test mode, the device records an ECG signal over a predetermined time interval.

Figure 3:
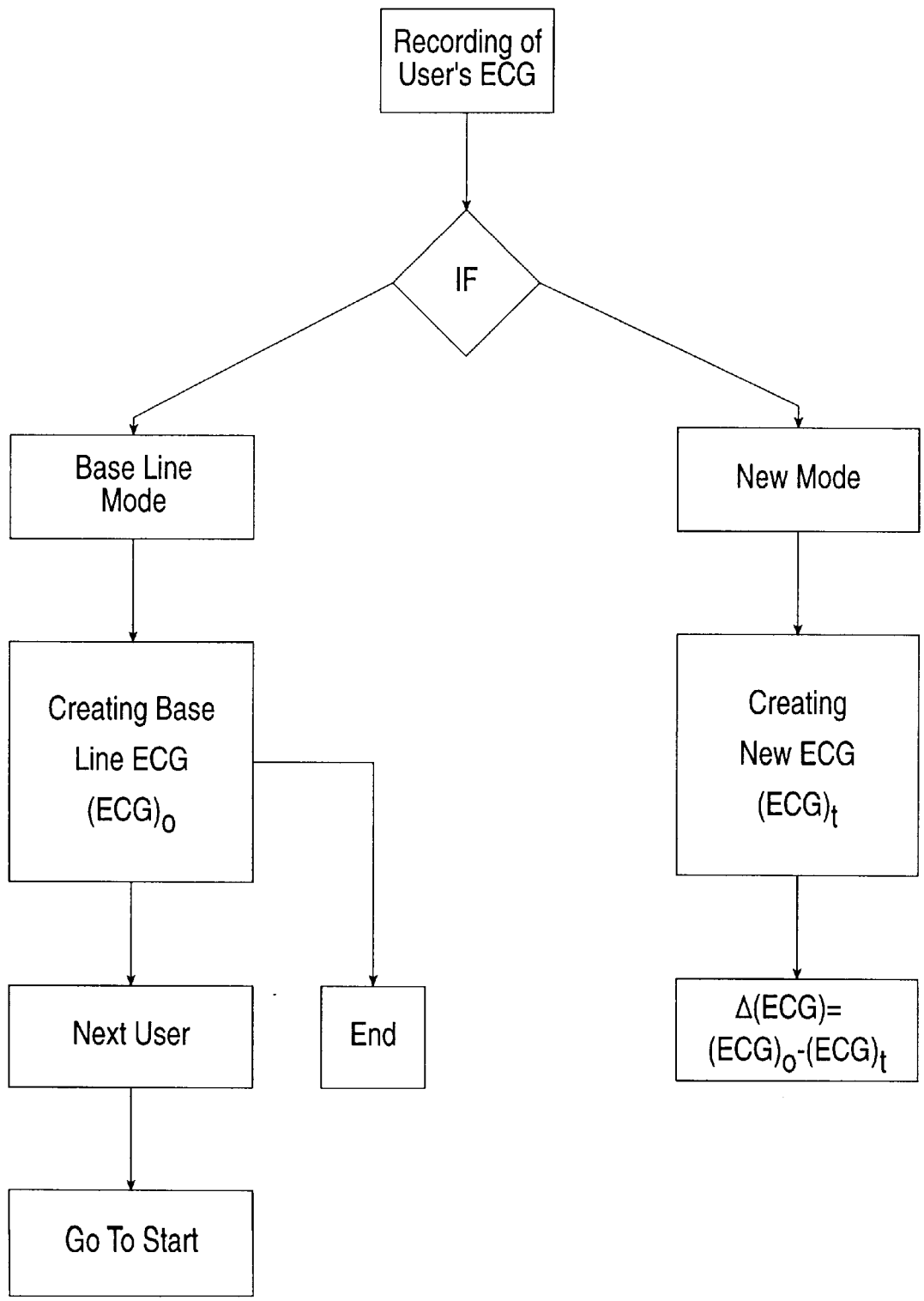
FIG. 3 is a schematic block diagram which illustrates a preferred second step of a method according to the present invention including selection between a base line mode and a new mode.

FIG. 3 illustrates a preferred procedure of recording an ECG signal. Display unit 20 asks the user if he is currently recording a base line (reference) mode or a new (real time examined) mode. The user uses keyboard unit 18 to select a the required mode. If the user selects a base line mode, the device preferably records twelve base line ECG signals and stores the information within long term permanent memory of signal processing unit 26. Signal processing unit 26 employs signal processing algorithms and statistical analysis methods for determining the values of selected ECG parameters for each of the twelve ECG signals. The selected parameters preferably includes: (a) ST level of each signal (measured in mm); (b) the sign of T wave of each signal; (c) the amplitude of Q wave of each signal (measured in mm); (d) the width of Q wave of each signal (measured in msec); (e) R-apex (measured in mm); (f) heart rate (measured per min); and (g) heart rhythm.

Preferably, for determining the ST level of an ECG signal, processing unit 26 averages the values of ST levels over a predetermined time interval.

When determining the sign of T wave parameter, the following procedure is preferably carried out: if the T wave has a positive amplitude then the sign of T wave parameter is determined to be a certain positive number, preferably +1; if the T wave has a negative amplitude then the sign of T wave parameter is determined to be the same negative number, preferably -1.

Preferably, the location of the R-apex is used so as to identify the location of a specific QRS complex. Since there are many artifacts in the ECG signal, a method for accurately identifying and locating the R-apex of a QRS complex is needed. The present invention provides a novel method for estimating the location of the R-apex component of a QRS complex recorded during a specific time interval. The method preferably includes: (a) finding the R-apex location of each of the QRS complexes in a specific ECG signal by means of conventional methods, wherein each ECG signal preferably represent a specific lead; (b) performing such procedure for each of the twelve ECG signals; (c) arranging the results within a matrix wherein each of the matrix's rows relates to a specific ECG signal, and wherein each of the matrices's columns relates to a specific QRS complex recorded during a specific time interval; and (d) performing the following procedure for each of the columns: if at least preferably four R-apex locations are within a predetermined time range, then the R-apex location of the specific QRS complex represented by the column is estimated to be an average of the four locations. Preferably, the predetermined time range is 0.1 seconds.

Signal processing unit 26 preferably further calculates secondary parameters such as J-point and R-apex location. All the calculated parameters are stored within memory elements for further processing.

After recording twelve base line ECG signals from a specific user, display unit 20 asks if the procedure should be repeated for the next user.

When the user selects a new (real time) mode for recording examined ECG signals, the device preferably records twelve new ECG signals and stores the information within signal processing unit 26. Signal processing unit 26 employs signal processing algorithms and statistical methods for determining the values of selected EGG parameters for each of the twelve ECG signals. The selected parameters preferably includes: (a) ST level of each signal; (b) the sign of T wave of each signal; (c) the amplitude of Q wave of each signal; (d) the width of Q wave of each signal; (e) R-apex (f) heart rate; and (g) heart rhythm.

Signal processing unit 26 preferably calculates secondary parameters such as J-point and R-apex location. All the calculated parameters are stored within memory elements for further processing.

Immediately after recording twelve new ECG signals, comparison system 28 compares each of the twelve new ECG signals to the respective base line ECG signal. The comparison is performed for each of the calculated parameters preferably by subtracting the parameters of a new ECG signal (new parameters) from the respective parameters of a base line ECG signal (base line parameters). The comparison of new parameters to base line parameters is performed for each of the twelve ECG signals so as to produce twelve delta values for each parameter. The results of the subtraction (the delta values) are stored within memory elements for further processing.

Figure 4:
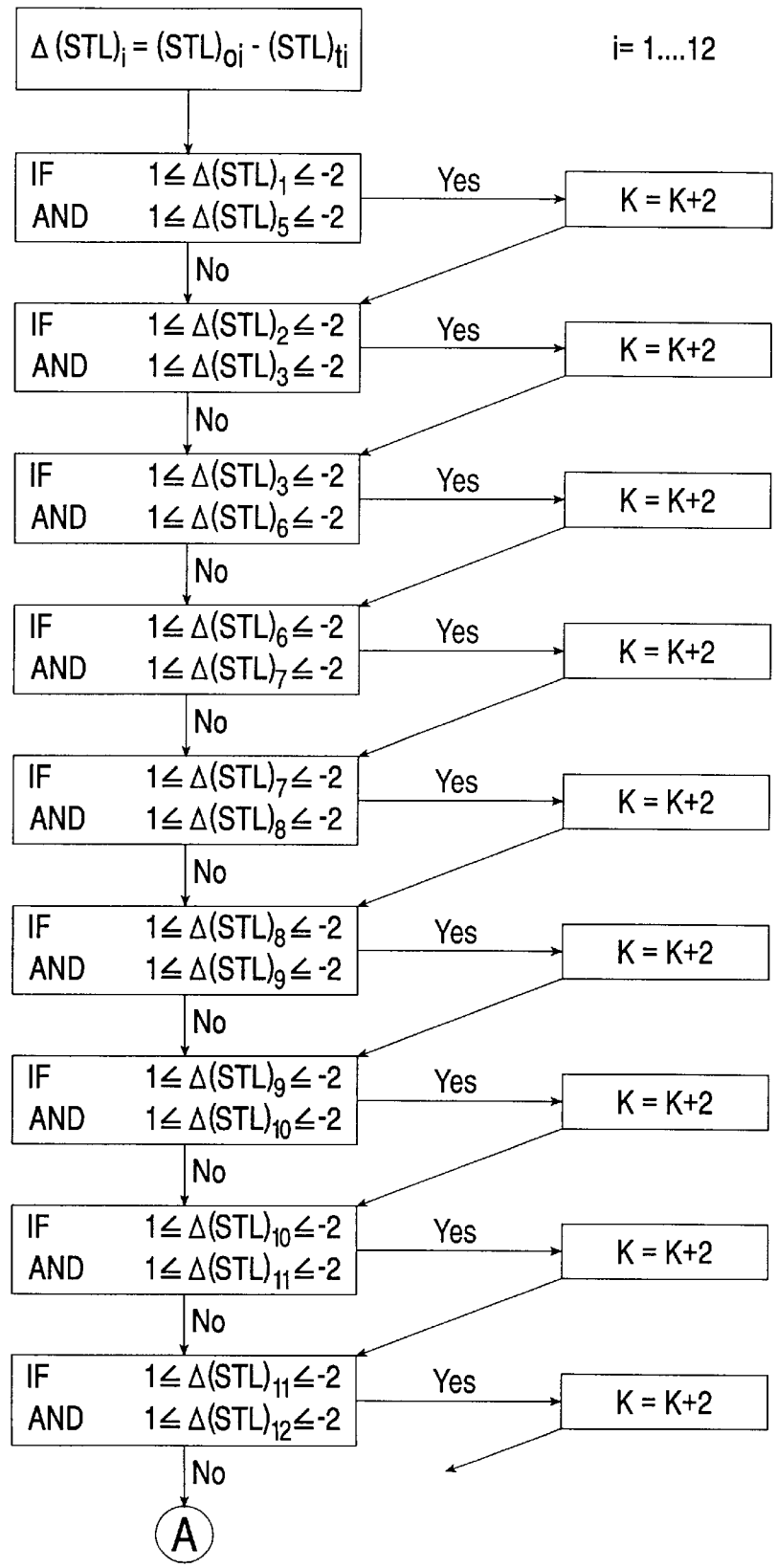
FIG 4 is a schematic block diagram which illustrates a preferred step of a method according to the present invention including an analysis based on comparison of the ST level of a base line signal to the ST level of a new signal.

FIG. 4 illustrates a preferred procedure for analysis of twelve delta values of the ST level parameter obtained by subtracting twelve new parameters from respective twelve base line parameters.

Specifically, the lead number is designated as i, wherein i=1,2, ... 12; base line information is designated as 0; real time (new information) is designated as t; a delta value is designated as $\Delta$; and the ST level parameter is designates as STL.

The twelve delta values refer to the twelve ECG signals commonly designated as: I, II, III, (AVR), (AVL), (AVF), V1, V2, V3, V4, V5 and V6, and are designated in FIG. 4 as: 1, 2, 3, 4, 5, 6, 7, 8, 9, 10, 11, and 12, respectively.

After obtaining twelve delta values referring to the ST level parameter (designated as STL), logical decision unit 30 analyzes distinct pairs of the delta values. Preferably, the distinct pairs includes adjacent leads. The analysis performed by logical decision unit 30 preferably includes the following procedure: If the delta value for a given lead is above a predetermined positive threshold value or below a predetermined negative threshold value and the delta value for another lead is above the predetermined positive threshold value or below the predetermined negative threshold value, then the examined parameter (ST level) has been substantially changed. The threshold values are preferably measures in mm. Preferably, the positive threshold value is 1mm and the negative threshold value is −2 mm (see also FIG. 8).

The indication of such substantial change is preferably counted and accumulated within a storing variable K. Preferably, if a substantial change has been indicated in the value of a specific parameter, then K=K+2.

As shown in the figure, the above analysis is preferably performed for each of the following pairs: leads 1 and 5; leads 2 and 3, leads 3 and 6; leads 6 and 7; leads 7 and 8; leads 8 and 9; leads 9 and 10; leads 10 and 11; and leads 11 and 12.

The final value of K is examined in the last step of the procedure (FIG. 6) for making a final decision by logical decision unit 30.

Figure 5:
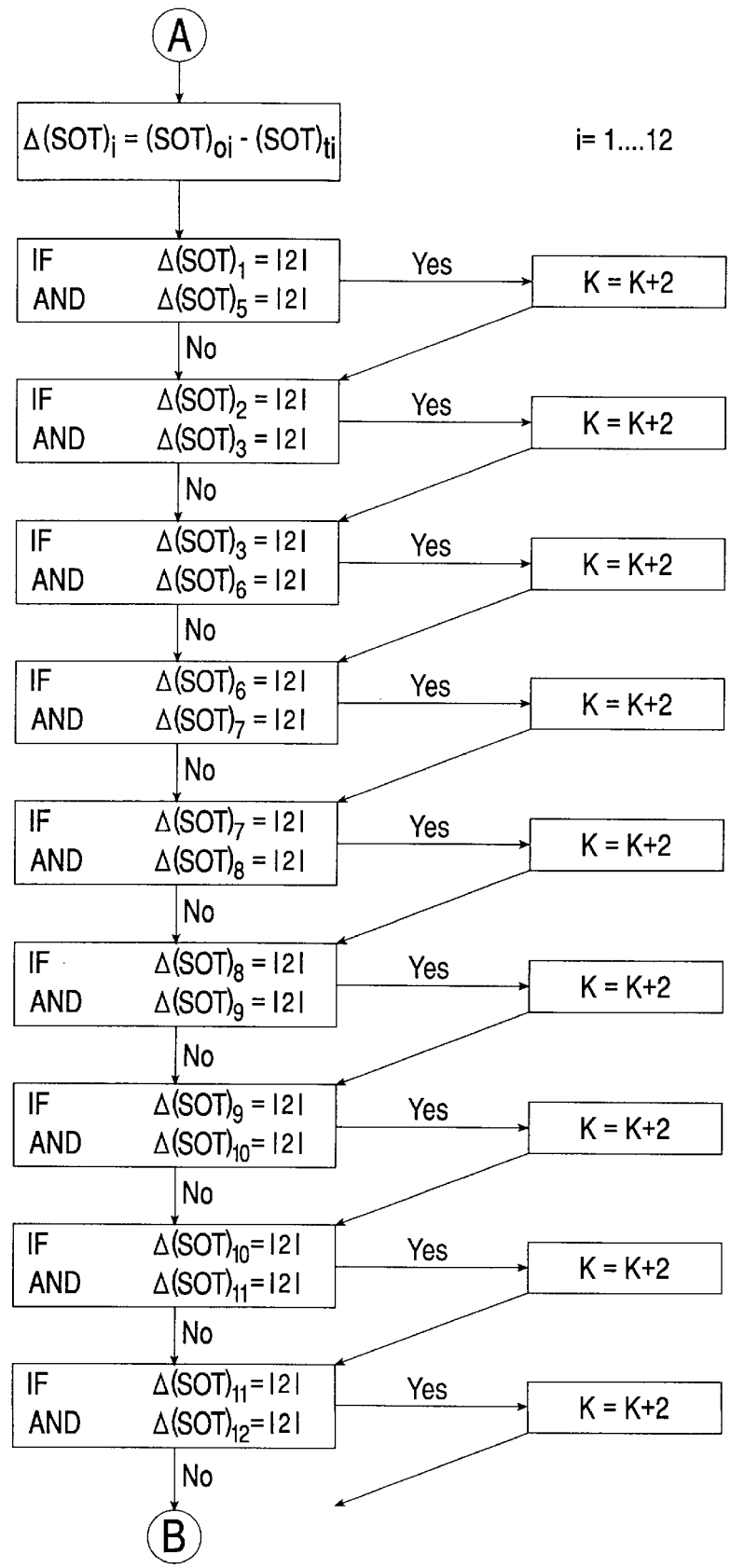
FIG. 5 is a schematic block diagram which illustrates a preferred step of a method according to the present invention including an analysis based on the examination of a T-wave inversion in the new signal relative to the base line signal.

FIG. 5 illustrates a preferred procedure for analysis of twelve delta values of the sign of T wave parameter (designated as SOT) obtained by subtracting twelve new parameters from respective twelve base line parameters. Since the sign of T wave parameter can accept the values of +1 or −1, the delta values referring to this parameter can accept the values of 0 (no change in the sign of T wave) or |2| (an inversion of the T wave). see also FIG. 8.

As in FIG. 4, the twelve delta values refer to the twelve ECG signals (leads) commonly designated as: I, II, III, (AVR), (AVL), (AVF), V1, V2, V3, V4, V5 and V6, and are designated in the figure as: 1, 2, 3, 4, 5, 6, 7, 8, 9, 10, 11, and 12 respectively.

After obtaining twelve delta values referring to the sign of T wave parameter (designated as SOT), logical decision unit 30 analyzes distinct pairs of the delta values. Preferably, the distinct pairs includes adjacent leads. The analysis performed by logical decision unit 30 preferably includes the following procedure: If the delta value for a given lead is |2| (the absolute value of 2) and the delta value for another within the selected pair lead is |2|, then the examined parameter (SOT) has been substantially changed.

The indication of such change is preferably counted and accumulated within storing variable K. If a substantial change has been indicated in the value of SOT, then K=K+2.

As shown in the figure, the above analysis is preferably performed for each of the following pairs: leads 1 and 5; leads 2 and 3, leads 3 and 6; leads 6 and 7; leads 7 and 8; leads 8 and 9; leads 9 and 10; leads 10 and 11; and leads 11 and 12.

FIG. 6 summarizes preferred procedures for analyzing ECG signals based on the following parameters: (a) the ST level parameter (designated as STL and measured in mm); (b) sign of T wave parameter (designated as SOT); (c) width of Q wave (designated as QInt and measured in msec); amplitude of Q wave (designated as Qamp and measured in mm); and amplitude of R wave (designated as Ramp and measured in mm); (d) heart rate (designated as Rate and measured per min) and (e) heart rhythm (designated as ARTH).

The detailed preferred procedures for analyzing the ECG signals based on the ST level parameter (STL) and the sign of T wave parameter (SOT) have been already described in FIGS. 4 and 5 and accompanying written description.

A preferred procedure for analyzing the ECG signals based on the width of Q wave (QInt), amplitude of Q wave (Qamp) and amplitude of R wave (Ramp) is as follows: twelve delta values of the width of Q wave parameter (QInt) are obtained by subtracting twelve base line parameters from respective twelve new parameters.

After obtaining twelve delta values referring to the width of Q wave parameter, logical decision unit 30 analyzes distinct pairs of the delta values. Preferably, the distinct pairs includes adjacent leads. The analysis performed by logical decision unit 30 preferably includes the following procedure: (i) If the delta value of the QInt parameter is above a predetermined threshold value for a given lead; and (ii) if the new (real time) Qamp parameter is greater than a fraction of the new (real time) Ramp parameter for the same lead, and such conditions are met for two leads of a selected pair, then the examined (real time) signal has been substantially changed relative to the base line signal. The threshold value is preferably 30 msec. The fraction is preferably 0.5.

The indication of such substantial change is preferably counted and accumulated within storing variable K. Preferably, if a substantial change has been indicated in the examined (real time) signal, then K=K+2.

A preferred procedure for analyzing the ECG signals based on the heart rate is as follows: if the heart rate provided by a new (real time) ECG signal is higher than a maximum threshold value or lower than a minimum threshold value then K=K+2. Preferably, the maximum threshold value is 150 pulses per min and the minimum threshold value is 40 pulses per min.

A preferred procedure for analyzing the ECG signals based on heart rhythm (ARTH) is as follows: a delta value of the ARTH parameter for a given lead is obtained by dividing a new (real time) parameter by respective base line parameter. After obtaining a delta value referring to the ARTH parameter, logical decision unit 30 analyzes the delta value preferably according to the following procedure: (i) If the delta value of the ARTH parameter is above a predetermined threshold value, then the examined (real time) parameter has been substantially changed relative to the base line parameter. The threshold value is preferably 2.

Preferably, if a substantial change has been indicated in the examined (real time) signal, then K=K+2.

Figure 7:
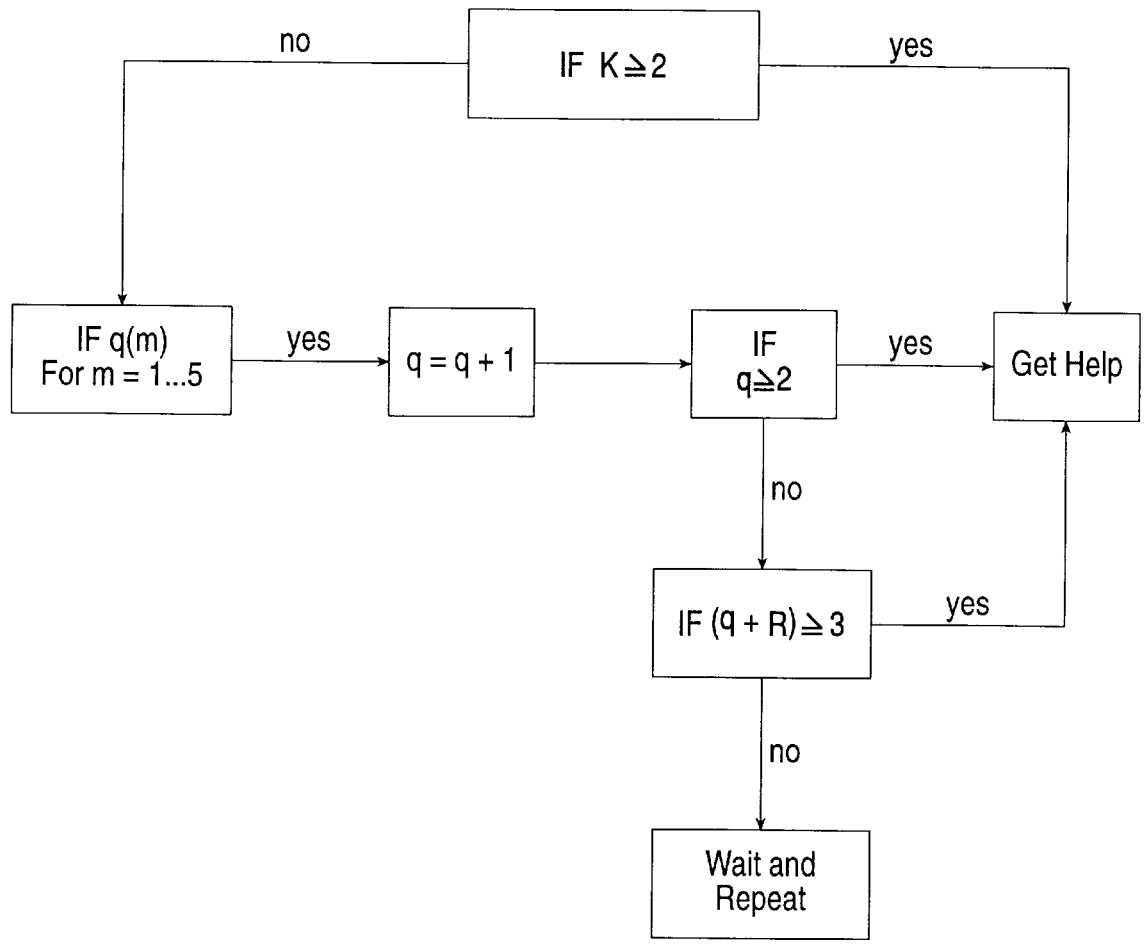
FIG. 7 is a schematic block diagram which illustrates a preferred last step of a method according to the present invention including a decision making step based on the examination of accumulated changes between the base line signal and the new signal as well as on other information interactively provided by the patient.

FIG. 7 illustrates a preferred last step of a method according to the present invention including a decision making step performed by logical decision unit 30 based on the examination of accumulated changes between the base line signals and the new signals as well as on other information interactively provided by the patient.

Specifically, if the value of K is at least 2, display unit 20 immediately recommends the user to get medical advice. If the value of K is smaller than 2, display unit 20 asks the user a list of questions designated as qm, wherein preferably m=1, . . 5. The questions may be, for example: do you sweat?; do you have breathing difficulties; and the like. If the answer to a presented answer is positive, then the information is accumulated within a storing variable q. Preferably, if the answer to a given question is positive, then q=q+1.

If the user has positively answered to at least a predetermined number of questions, then display unit 20 recommends the user to get medical advice. Preferably, if the user has positively answered to at least two questions, then the value of q is at least 2 and the user is advised to get medical advice. If the value of q is smaller than 2, then the risk factor R is taken into account. For example, if the sum of R and q is at least 3, then the user is advised to get medical advice. If the sum of R and q is smaller than 3, then display unit 20 recommends the user to wait a certain period of time, for example 30 min, and repeat the procedure. If the results of the second examination indicates that no significant changes or abnormal symptoms have been found, then display unit 20 notifies the user that no problematic signs have been identified.

Preferably, a method and device according to the present invention may be used with Holter device so as to automatically detect and analyze erratic changes found, for example, in "silent ischemia".

While the invention has been described with respect to a limited number of embodiments, it will be appreciated that many variations, modifications and other applications of the invention may be made.

What is claimed is:

1. A method of a user's ECG self monitoring and analysis, the method comprising the steps of:
   (a) recording and storing a first ECG signal from the user during a first time interval;
   (b) recording a second ECG signal from the user during a second time interval;
   (c) analyzing said ECG signals by comparing said second ECG signal to said first ECG signal thereby obtaining a comparison of said first and second ECG signals; and
   (d) based on said analysis and comparison, making a logical decision and providing a recommendation to the user of a step the user should take.

2. The method of claim 1, further comprising the step of calculating a first ECG parameter of said first ECG signal and a second respective ECG parameter of said second ECG signal and wherein said comparison is performed by comparing said first and second ECG parameters.

3. The method of claim 2, wherein said first and second ECG parameters are selected from the group consisting of a ST level parameter derived from said first and second ECG signals, a sign of a T-wave parameter derived from said first and second ECG signals, an amplitude of a Q wave parameter derived from said first and second ECG signals, a width of a Q wave parameter derived from said first and second ECG signals, an amplitude of a R wave parameter derived from said first and second ECG signals, a heart rate parameter derived from said first and second ECG signals and a heart rhythm parameter derived from said first and second ECG signals.

4. The method of claim 1, further comprising the step of:
   (e) interactively asking the user a list of questions being related to the user's medical status and requesting the user for answers to said questions;
wherein making said logical decision and providing said recommendation to the user of said step the user should take is effected based on said answers to said questions.

5. The method of claim 1, further comprising the step of:
   (e) determining a risk factor for the user;
wherein making said logical decision and providing said recommendation to the user of said step the user should take is effected based on said risk factor.

6. A method of user's ECG self-monitoring and analysis, the method comprising the steps of:
   (a) simultaneously recording twelve ECG signals from the user during a first time interval by using ten sensors;
   (b) simultaneously recording twelve ECG signals from the user during a second time interval;
   (c) analyzing said ECG signals by comparing each of said ECG signals recorded during said second time interval to a respective ECG signal recorded during said first time interval so as to provide twelve delta values of comparison; and (d) based on said analysis and comparison, making a logical decision and providing a recommendation to the user of a step the user should take.

7. The method of claim 6, further comprising the step of:
   (e) prior to, and for effecting, the step of making said logical decision and providing said recommendation, analyzing a number of specific pairs of said delta values of comparison.

8. The method of claim 7, wherein said twelve ECG signals recorded during said first said second time intervals are I ECG signals, II ECG signals, III ECG signals, (AVR) ECG signals, (AVL) ECG signals, (AVF) ECG signals, V1 ECG signals, V2 ECG signals, V3 ECG signals, V4 ECG signals, V5 ECG signals and V6 ECG signals, and further wherein said specific pairs of said delta values of comparison are selected from the group consisting of delta values of said I ECG signals and said (AVL) ECG signals, delta values of said II ECG signals and said III ECG signals, delta values of said III ECG signals and said (AVF) ECG signals, delta values of said (AVF) ECG signals and said V1 ECG signals, delta values of said V1 ECG signals and said V2 ECG signals, delta values of said V2 ECG signals and said V3 ECG signals, delta values of said V3 ECG signals and said V4 ECG signals, delta values of said V4 ECG signals and said V5 ECG signals and delta values of said V5 ECG signals and said V6 ECG signals.

9. The method of claim 7, further comprising the step of calculating an ECG parameter of each of said twelve ECG signals recorded during said first time interval and a respective ECG parameter of each of said twelve ECG signals recorded during said second time interval and wherein the step of analyzing said ECG signals is effected by comparing said ECG parameters to said respective ECG parameters.

10. The method of claim 9, wherein said ECG parameters and said respective ECG parameters are selected from the group consisting of a ST level parameter derived from said ECG signals, a sign of a T-wave parameter derived from said ECG signals, an amplitude of a Q wave parameter derived from said ECG signals, a width of a Q wave parameter derived from said ECG signals, an amplitude of a R wave parameter derived from said ECG signals, a heart rate parameter derived from said ECG signals and a heart rhythm parameter derived from said ECG signals.

11. The method of claim 6, further comprising the step of:
   (e) interactively asking the user a list of questions being related to the user's medical status and requesting the user for answers to said questions;
wherein making said logical decision and providing said recommendation to the user of said step the user should take is effected based on said answers to said questions.

12. The method of claim 6, further comprising the step of:
   (e) determining a risk factor for the user;
wherein making said logical decision and providing said recommendation to the user of said step the user should take is effected based on said risk factor.

13. The method of claim 6, further comprising the step of:
   (e) prior to, and for effecting, the step of making said logical decision and providing said recommendation, estimating R-apex locations of QRS complexes in said simultaneously recorded ECG signals, by:
      (i) finding said R-apex locations for each of said simultaneously recorded ECG signals, so as to obtain a matrix of said R-apex locations, said matrix being characterized in that each of said matrix's rows relates to a specific recorded ECG signal and each of said matrix's columns relates to a specific QRS complex;
      (ii) if at least a predetermined number of R-apex locations are within a predetermined time range, then estimating the R-apex location of said specific ECG complex to be within said predetermined time range; and (iii) based on said number of R-apex locations being within said predetermined time range, making said logical decision and providing said recommendation.

14. A device for user's ECG self monitoring and analysis, comprising:

(a) a sensing element and a processing element for recording and storing a first ECG signal from the user during a first time interval and recording a second ECG signal from the same user during a second time interval;

(b) a comparing element for analyzing said ECG signals by comparing said second ECG signal to said first ECG signal to thereby obtain a comparison of said first and second ECG signals; and (c) a logical decision element, which, based on said analysis and comparison, serves for logically evaluating said comparison, making a logical decision and for providing a recommendation to the user of a step the user should take.

15. The device of claim 14, wherein said processing element calculates a first ECG parameter of said first ECG signal and a second respective ECG parameter of said second ECG signal and said comparing element compares said first and second ECG parameters.

16. The device of claim 15, wherein said first and second ECG parameters are selected from the group consisting of a ST level parameter derived from said first and second ECG signals, a sign of a T-wave parameter derived from said first and second ECG signals, an amplitude of a Q wave parameter derived from said first and second ECG signals, a width of a Q wave parameter derived from said first and second ECG signals, an amplitude of a R wave parameter derived from said first and second ECG signals, a heart rate parameter derived from said first and second ECG signals and a heart rhythm parameter derived from said first and second ECG signals.

17. The device of claim 14, wherein said device includes a display element and a keyboard for interactively communicating with the user.

18. The device of claim 17, wherein said display element serves for asking the user a list of questions being related to the user's medical status, and wherein making said logical decision and providing said recommendation to the user by said logical decision element is effected by said logical decision element based on said answers to said questions.

19. The device of claim 17, wherein said device includes an instruction panel for instructing the user how to determine the user's risk factor.

20. The device of claim 19, wherein said display element displays a question to the user for the user's risk factor and said decision is made and said recommendation is given by said logical decision element based on said risk factor.

21. The device of claim 14, wherein said sensing element includes a plurality of sensors mechanically interconnected there amongst.

22. The device of claim 15, further comprising a stored information transferring element communicating with said processing element, so as to enable later analysis of said stored information.

23. The device of claim 15, further comprising elements for storing different personal codes for ECG examination, so as to enable ECG examination by different users.

24. A device of user's ECG self-monitoring and analysis, comprising:

(a) ten sensing elements and a processing element for simultaneously recording twelve ECG signals from the user during a first time interval and simultaneously recording twelve ECG signals from the user during a second time interval;

(b) a comparing element for analyzing said ECG signals by comparing each of said ECG signals recorded during said second time interval to a respective ECG signal recorded during said first time interval so as to provide twelve delta values of comparison; and (c) a logical decision element, which, based on said analysis and comparison, serves for logically evaluating said comparison, making a logical decision and for providing a recommendation to the user of a step the user should take.

25. The device of claim 24, wherein said logical decision element, prior to, and for effecting making said logical decision and providing said recommendation, serves for analyzing a number of specific pairs of said delta values of comparison.

26. The device of claim 25, wherein said twelve ECG signals recorded during said first said second time intervals are I ECG signals, II ECG signals, III ECG signals, (AVR) ECG signals, (AVL) ECG signals, (AVF) ECG signals, V1 ECG signals, V2 ECG signals, V3 ECG signals, V4 ECG signals, V5 ECG signals and V6 ECG signals, and further wherein said specific pairs of said delta values of comparison are selected from the group consisting of delta values of said I ECG signals and said (AVL) ECG signals, delta values of said II ECG signals and said III ECG signals, delta values of said III ECG signals and said (AVF) ECG signals, delta values of said (AVF) ECG signals and said V1 ECG signals, delta values of said V1 ECG signals and said V2 ECG signals, delta values of said V2 ECG signals and said V3 ECG signals, delta values of said V3 ECG signals and said V4 ECG signals, delta values of said V4 ECG signals and said V5 ECG signals and delta values of said V5 ECG signals and said V6 ECG signals.

27. The device of claim 26, further comprising an instruction panel for instructing the user how to determine the user's risk factor.

28. The device of claim 25, wherein said display element serves for asking the user a list of questions being related to the user's medical status, and wherein making said logical decision and providing said recommendation to the user by said logical decision element is effected based on said answers to said questions.

29. The device of claim 24, wherein said processing element calculates an ECG parameter of each of said twelve ECG signals recorded during said first time interval and a respective ECG parameter of each of said twelve ECG signals recorded during said second time interval and wherein said twelve delta values are calculated by comparing said ECG parameters to said respective ECG parameters.

30. The device of claim 29, wherein said ECG parameters and said respective ECG parameters are selected from the group consisting of a ST level parameter derived from said ECG signals, a sign of a T-wave parameter derived from said ECG signals, an amplitude of a Q wave parameter derived from said ECG signals, a width of a Q wave parameter derived from said ECG signals, an amplitude of a R wave parameter derived from said ECG signals, a heart rate parameter derived from said ECG signals and a heart rhythm parameter derived from said ECG signals.

31. The device of claim 29, wherein said display element displays a question to the user for the user's risk factor and said decision is made and said recommendation is given by said logical decision element based on said risk factor.

32. The device of claim 24, wherein said device includes a display element and a keyboard for interactively communicating with the user.

33. The device of claim 24, wherein said ten sensing elements are mechanically interconnected there amongst.

34. The device of claim 24, further comprising a stored information transferring element communicating with said processing element, so as to enable later analysis of said stored information.

35. The device of claim 24, further including elements for storing different personal codes for ECG examination, so as to enable ECG examination by different users.

* * * * *